United States Patent [19]

Reichel

[11] Patent Number: 4,505,175

[45] Date of Patent: Mar. 19, 1985

[54] MICROTOME

[75] Inventor: Artur Reichel, Wetzlar, Fed. Rep. of Germany

[73] Assignee: Ernst Leitz Wetzlar GmbH, Wetzlar, Fed. Rep. of Germany

[21] Appl. No.: 568,884

[22] Filed: Jan. 6, 1984

[30] Foreign Application Priority Data

Jan. 21, 1983 [DE] Fed. Rep. of Germany ....... 3301921

[51] Int. Cl.³ ............................................. G01N 1/06
[52] U.S. Cl. ........................................ 83/703; 83/564; 83/713; 83/734; 83/915.5
[58] Field of Search ..................... 83/915.5, 703, 563, 83/564, 426, 433, 734, 713

[56] References Cited

U.S. PATENT DOCUMENTS 3,030,992  4/1962  Picard ............................... 83/734 X
3,293,972  12/1966 Burkhardt et al. ................ 83/703 X
3,828,641  8/1974  Sitte ..................................... 83/703
4,126,069  11/1978 Shimonaka ............................ 83/703

FOREIGN PATENT DOCUMENTS 1117900  11/1961  Fed. Rep. of Germany ..... 83/915.5

Primary Examiner—Donald R. Schran
Attorney, Agent, or Firm—Schwartz, Jeffery, Schwaab, Mack, Blumenthal & Koch

[57] ABSTRACT

The microtome has a specimen slide moved periodically by a drive shaft, and a blade bracket comprising a blade slide and a blade holder. A threaded spindle serves to advance the blade bracket and thus the blade. The blade is retracted from the specimen after each cutting process, independently of the advance of the blade slide. For this purpose, the blade holder is merely tilted slightly by being raised around an axis, which forms an acute angle with the cutting edge of the blade. The blade holder is raised by a lever arrangement, coupled through a shaft and a pivot bearing with the drive shaft of the specimen slide.

9 Claims, 3 Drawing Figures

MICROTOME

BACKGROUND OF THE INVENTION

The present invention relates to a microtome having a specimen slide for moving a specimen periodically with respect to a blade. More particularly, the present invention relates to a specimen slide controlled by a drive shaft, and a blade holder carrying the blade and arranged on a blade slide horizontally displaceable by means of a threaded spindle to advance the blade, whereby the cutting process is effected during the movement of the specimen slide in the direction of the blade and the retraction of the blade takes place in the opposite direction.

A microtome is disclosed in DE P No. 1 117 900 in which the specimen holder may be moved periodically upwardly and downwardly and wherein the cutting process takes place during the downward stroke. A device is provided for the retraction of the cutting element from the specimen during the upward stroke. This retraction of the blade prevents damage to the specimen and is effected in this known microtome by the specimen holder and the cutting element being arranged on a common pedestal. An electromagnetic device serves as the retracting means and elastically deforms the pedestal whereby the cutting element is retracted from the path of the specimen when the specimen holder moves upwardwardly into its initial position. The retracting device is connected with a control device which also controls an electrodynamic device to move the specimen holder.

WO No. 81/02063 discloses a rotating microtome, the advance whereof is transmitted by a spindle to a parallelogram guide which carries the specimen holder. The joints of the parallelogram guide are formed by a plurality of flexural pivots. As a result of the use of spring elements, this guide tends to vibrate and retracts on the specimen side with a corresponding movement of the springingly supported mass of the specimen holder.

SUMMARY OF THE INVENTION

It is an object of the present invention to provide a microtome having a blade which can be retracted in its return stroke in order that the thickness of the cut to be effected can be reproducibly set.

Another object of the present invention is to provide a microtome wherein the retraction of the blade is effected separately from the advance of the blade slide and thus takes place without the application of a large force in a practically vibration-free manner.

A further object of the present invention is to provide a microtome which is not restricted to use with small specimens and requires only a minimal expense.

In accomplishing the foregoing objects, there has been provided in accordance with the present invention a microtome, comprising: a blade; a blade holder carrying the blade; a blade slide, with the blade holder being displaceably mounted on the blade slide; means for moving the blade holder horizontally on the blade slide; a specimen slide; means for moving the specimen slide periodically toward the blade and away from the blade; and means, drivingly connected with the specimen slide moving means, for rotating the blade holder vertically around an axis which forms an acute angle with the cutting edge of the blade, independently of the blade slide moving means.

In this manner, the entire blade holder, which is difficult to move as a result of its arcuate fitting, does not have to perform a retracting motion corresponding to the thickness of the cut in addition its advance movement in order to subsequently pass through the defined advance.

BRIEF DESCRIPTION OF THE DRAWINGS

Further objects, features and advantages of the invention will become apparent from the detailed description of preferred embodiments below, reference being had to the accompanying drawings in which like reference numerals represent like parts throughout and in which.

DETAILED DESCRIPTION OF PREFERRED EMBODIMENTS

Figure 1:
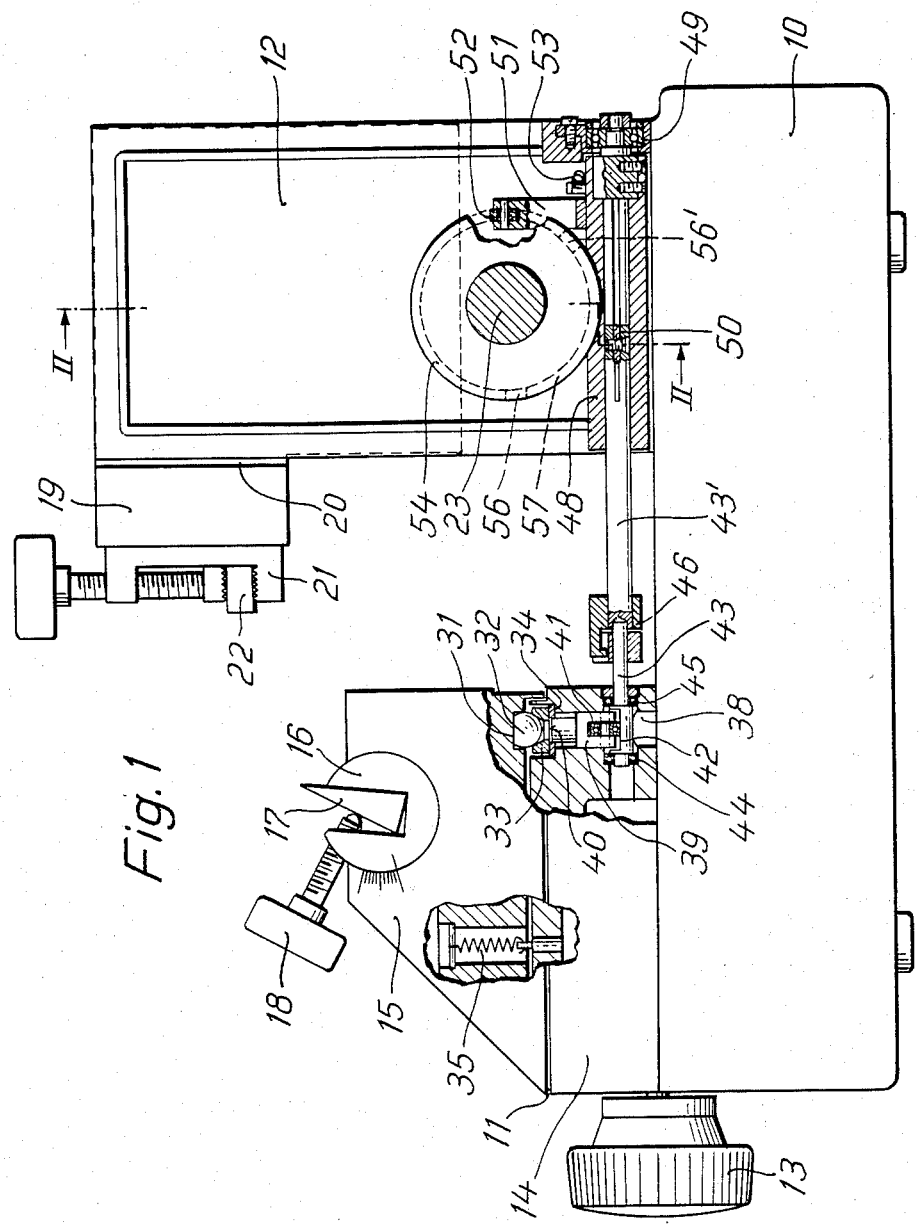
FIG. 1 shows a lateral sectional elevation of the microtome according to the present invention.

The rotating microtome shown in FIG. 1 consists essentially of a base 10, upon which a blade bracket 11 is displaceably mounted and a specimen slide holder 12 is rigidly mounted. The blade bracket 11 is adjustable by means of a knurled wheel 13. The bracket 11 consists of a blade slide 14 which is movable with respect to the base 10, and a blade holder 15 which is supported by the blade slide. The base 10 of the microtome comprises a known advance mechanism (not shown) with coarse and fine adjusting means for the blade bracket 11. In the blade holder 15, dual cylinderical blade clamps 16 are rotatingly supported. A blade 17 is mounted in clamps 16 and may be immobilized by means of thumb screws 18.

Figure 2:
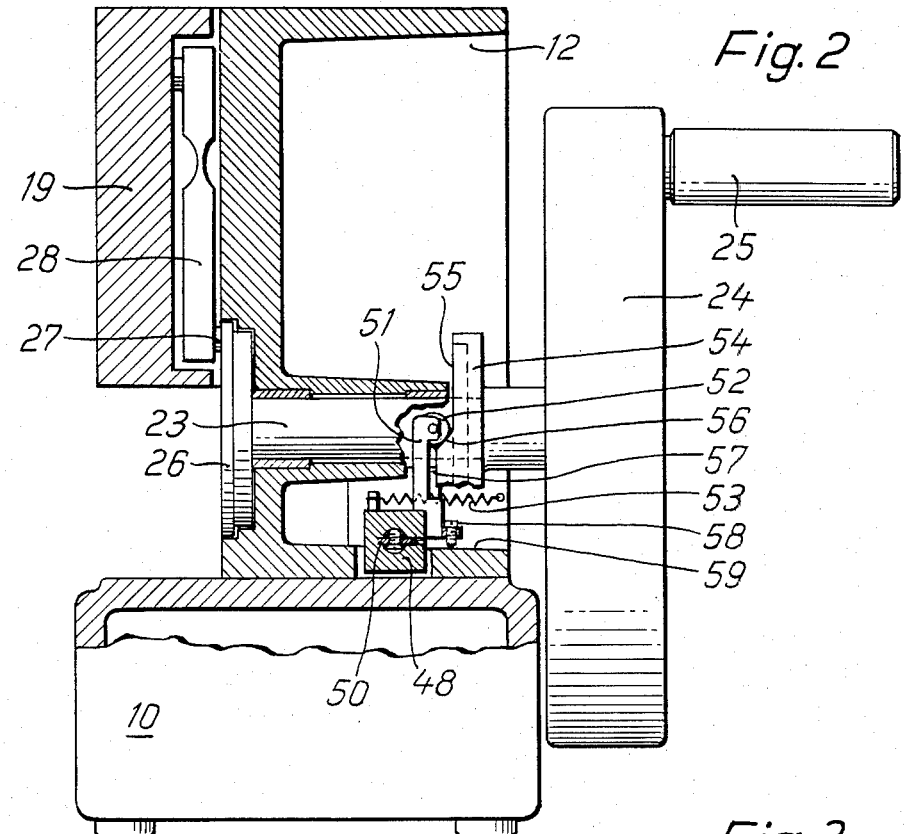
FIG. 2 shows a sectional view along the line II—II of FIG. 1.

In the specimen slide holder 12, a specimen slide 19 may be moved periodically up and down in a slide guide 20. The specimen slide 19 carries a specimen clamp 21 to receive a specimen 22. The specimen slide 19 is driven by a drive shaft 23, upon which a hand wheel 24 is mounted (FIG. 2). A handle 25 is rigidly mounted to the hand wheel 24. To the end of the drive shaft 23 facing away from the hand wheel 24, a washer 26 is rigidly fastened. Washer 26 engages a connecting rod 28 through an eccentrically mounted bolt 27. Connecting rod 28 moves the specimen slide 19 in a known manner.

Figure 3:
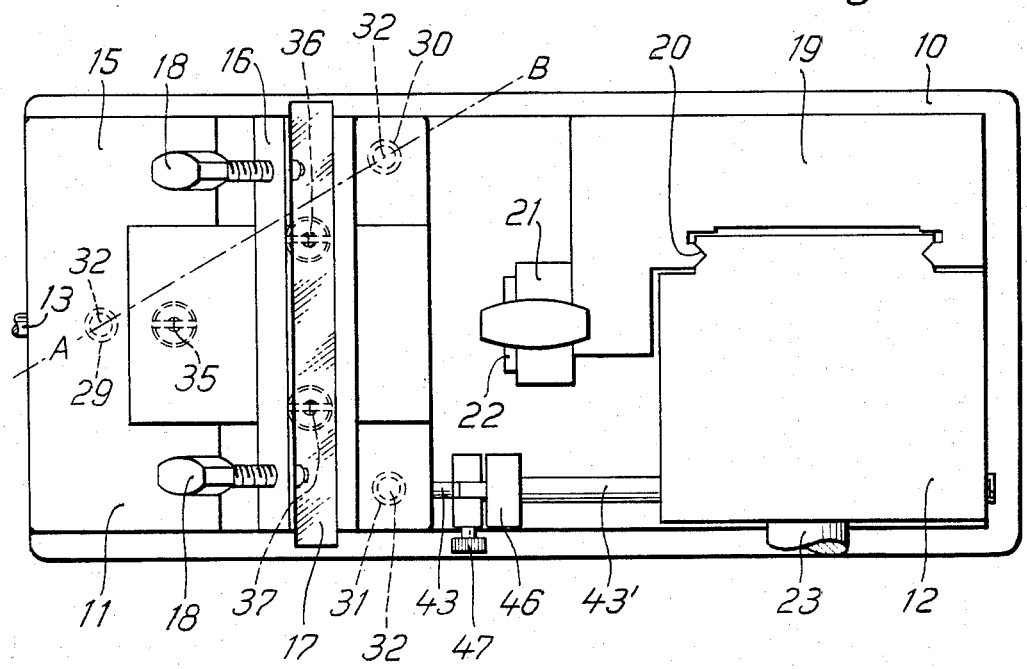
FIG. 3 shows a top view of the microtome.

A three point base comprising support points 29, 30 and 31 (FIGS. 1 and 3) is arranged between the blade holder 15 and the blade slide 14. The three point base comprises flattened spheres and ball sockets. For the sake of clarity only the support point 31 with the sphere 32 and the ball socket 33 is shown in detail in FIG. 1. In place of the sphere and ball socket, other known supporting elements, such as cylindrical rollers and V bearings, may be used. While the spheres of all of the support points 29, 30, 31 are fixedly joined with their flattened surface to the blade holder 15, for example, by adhesive bonding, only the ball sockets of the two supports 29, 30 are connected with the blade slide 14. The ball socket of the third support point 31, on the other hand, is freely displaceable on a support disk 34. Support disk 34 is fixedly joined to the blade slide 14 and is centered by the sphere 32 on the blade holder 15. The blade holder 15 is drawn onto the blade slide 14 by tension springs 35, 36, 37.

Under the support point 31, a bore hole 38 is provided. A forked bolt 39 is slidingly supported in bore hole 38. The forked bolt 39 has a tapering upper section penetrating the support disk 34 and being guided by it. A planar surface 40 formed by the tapering upper section of the forked bolt 39 abuts against the ball socket 33. In the lower, forked section of the forked bolt 39, a ball bearing 41 is located. Ball bearing 41 has an external race, the external surface of which rests on a flattened area 42 of the shaft 43. Shaft 43 is held in two further ball bearings 44, 45, which are mounted on either side of the ball bearing 14. In order to compensate for alignment errors between the ball bearing 14 and the slide guide 20 of the specimen slide 19, the shaft 43 is not of a single piece, but is composed of partial shafts 43, 43'. To join the two partial shafts 43, 43', an angularly flexible and torsionally rigid coupling 46 is provided. Coupling 46 is readily separated by means of a knurled screw 47. The coupling 46 also forms a support for a pivot bearing 48. Pivot bearing 48 has a square cross section. Another support for pivot bearing 48 consists of a self-aligning ball bearing 49.

The partial shaft 43' may be displaced through a driver 50 which is telescopically received in the pivot bearing 48. This telescopic connection is provided to compensate for distance variations between the blade slide 1 and the specimen slide holder 12. In addition, coupling 46 can be separated and partial shaft 43' can be retracted from pivot bearing 48 so that the sliding surface under the pivot bearing 48 is more accessible for cleaning and maintenance.

A rocking lever 51 is fixedly connected perpendicularly to the pivot bearing 48. The rocking lever 51 carries a ball bearing 52 (FIG. 2) on its upper end. Ball bearing 52 abuts against the inner surface of a control disk 54. A tension spring 53 applied to the pivot bearing 48 elastically biases bearing 52 against the annular inner surface of control disk 54. Control disk 54 is fixedly mounted on the drive shfat 23 of the specimen slide 19. The control surface of the control disk 54 comprises a base surface 55 and a raised functional surface 57 connected with the surface 55 through bevels 56, 56'. Surface 57 is located parallel to and higher than the base surface 57. For angular adjustments of both the pivot bearing 48 and the rocking lever 51, an adjusting screw 58 is fastened to the pivot bearing 48. The adjusting screw is adjustable against a stop 59, mounted stationarily on the housing.

The mode of operation of the microtome described hereinabove is as follows.

Upon the rotation of the hand wheel 24 in the clockwise direction, the specimen slide 19 moves, together with the specimen 22, in the slide guide 20 from its uppermost position downwardly. During this downward stroke, the cut is performed, and the rocking lever 51 is located directly under the base surface 55 of the control disk 54. When the specimen slide 19 has attained its lowest position, the control disk 54 occupies a position in which the ball bearing 52 arrives on the bevel, the pivot bearing 48 is rotated by the rocking lever through a certain angle and held in this position as long as the ball bearing 52 rolls on the functional surface 57, i.e., during the entire idle (return) stroke of the specimen slide 19. The partial shaft 43' rotates through an angle which corresponds to the angular motion of the pivot bearing 48. The angular movement of partial shaft 42' is transmitted to the partial shaft 43 through the coupling 46. Since the ball bearing 4 of the forked bolt 39 rests on the flattened part 42 of the partial shaft 43, as partial shaft 43 rotates, the forked bolt is raised and forces ball socket 33 upwardly with its planar surface 40. Ball socket 33 in turn raises the sphere 32. As a result, the blade holder 15 is raised from its support point 31 and rotated around an axis A-B (FIG. 3), which is determined by the line connecting the two support points 29, 30. The cutting edge is thereby displaced in the horizontal direction so that the blade 17 no longer touches the already cut specimen 22 during the idle stroke of the specimen slide 19. Prior to attainment of its uppermost position by the specimen slide, the ball bearing of the rocking lever 51 slides from the functional surface 57 over the bevel 56' to a position immediately before the base surface 55. Correspondingly, the ball socket 33 comes to rest in the support point 31 on the bearing disk 34, and the blade holder 15 is again in the cutting position.

During the aforedescribed retraction of the blade, the cutting edge of the blade forms an angle with the surface of the specimen, but this angle may be neglected and the cutting edge of the blade within the section used may be considered parallel to the surface of the specimen at a distance of 50 to 60 microns.

The foregoing description is set forth for the purpose of illustrating the present invention, but is not deemed to be limiting. Clearly, numerous additions, substitutions and other changes may be made to the invention without departing from the scope thereof as set forth in the appended claims.

What is claimed is:

1. A microtome, comprising:
   a blade;
   a blade holder carrying said blade;
   a blade slide, said blade holder being displaceably mounted on said blade slide;
   means for moving said blade holder horizontally on said blade slide;
   a specimen slide;
   means for moving said specimen slide periodically toward said blade and away from said blade; and
   means drivingly connected with said specimen slide moving means for rotating said blade holder vertically around an axis which forms an accute angle with the cutting edge of said blade independently of said blade slide moving means.

2. A microtome according to claim 1, further comprising a 3-point support disposed between said blade holder and said blade slide for supporting said blade holder on said blade slide, and wherein said axis is defined by a line connecting to said 3 points, and wherein said 3 points define a triangle within which said cutting edge of said blade is located.

3. A microtome according to claim 1, further comprising tension springs connected between said blade holder and said blade slide for holding said blade holder on said blade slide.

4. A microtome according to claim 1, wherein said specimen slide moving means comprises a drive shaft, and wherein said means for rotating said blade holder comprises a control disk having functional surfaces formed thereon, and means responsive to said functional surfaces for pivoting said blade holder around said axis.

5. A microtome according to claim 4, wherein said pivoting means comprises a rocking lever held against said functional surfaces, and a pivoting shaft connected to be rotated by said rocking lever as said rocking lever follows said functional surfaces, and means for transforming said rotating motion of said pivoting shaft into vertical motion transmitted to a point on said blade holder spaced from said axis.

6. A microtome according to claim 5, wherein said means for transforming rotating motion comprises a flattened portion on said pivoting shaft, and a vertically displaceable member resting on said flattened portion, said vertically displaceable member contacting a lower portion of said blade holder.

7. A microtome according to claim 5, wherein said pivoting shaft comprises two sections.

8. A microtome according to claim 7, including an angularly flexible and torsionally rigid coupling connecting said two sections of said pivoting shaft.

9. A microtome according to claim 5, further comprising means for varying the length of said pivoting shaft.

* * * * *